United States Patent [19]

Chandraratna

[11] Patent Number: 5,344,959

[45] Date of Patent: Sep. 6, 1994

[54] TETRAHYDRONAPHTHYL AND CYCLOPROPYL SUBSTITUTED 1,3-BUTADIENES HAVING RETINOID-LIKE ACTIVITY

[75] Inventor: Roshantha A. Chandraratna, Mission Viejo, Calif.

[73] Assignee: Allergan, Inc., Irvine, Calif.

[21] Appl. No.: 63,540

[22] Filed: May 18, 1993

[51] Int. Cl.$^5$ .................. C07C 69/76; C07C 63/36
[52] U.S. Cl. .................. 560/100; 560/8; 560/10; 560/47; 560/51; 560/56; 560/64; 560/66; 562/427; 562/456; 562/458; 562/462; 562/466; 562/490; 564/162; 564/163; 564/171; 564/180; 568/38; 568/39; 568/632; 568/634; 585/26
[58] Field of Search .................. 560/8, 10, 47, 51, 56, 560/64, 66, 100; 562/427, 456, 458, 462, 466, 490; 564/163, 162, 171, 180; 568/38, 39, 632, 634; 585/26; 514/531, 569

[56] References Cited

U.S. PATENT DOCUMENTS

| | | | |
|---|---|---|---|
| 4,096,341 | 6/1978 | Frazer | 560/85 |
| 4,326,055 | 4/1982 | Loeliger | 542/429 |
| 4,391,731 | 7/1983 | Boller et al. | 252/299.62 |
| 4,695,649 | 9/1987 | Magami et al. | 560/86 |
| 4,723,028 | 2/1988 | Shudo | 560/8 |
| 4,739,098 | 4/1988 | Chandraratna | 560/8 |
| 4,740,519 | 4/1988 | Shroot et al. | 514/443 |
| 4,810,804 | 3/1989 | Chandraratna | 514/311 |
| 4,826,969 | 5/1989 | Maignan et al. | 536/55.2 |
| 4,855,320 | 8/1989 | Chatterjee et al. | 514/473 |
| 4,895,868 | 1/1990 | Chandraratna | 514/432 |
| 4,980,369 | 12/1990 | Chandraratna | 514/532 |

(List continued on next page.)

FOREIGN PATENT DOCUMENTS

| | | | |
|---|---|---|---|
| 0130795 | 1/1985 | European Pat. Off. | C07D 311/58 |
| 176034A | 4/1986 | European Pat. Off. | C07C 63/66 |
| 0284288 | 9/1988 | European Pat. Off. | C07D 401/04 |
| 0350846 | 7/1989 | European Pat. Off. | C07D 311/58 |
| 3708060 | 9/1987 | Fed. Rep. of Germany | C07D 311/04 |
| 2601670 | 1/1988 | France | |

OTHER PUBLICATIONS

A General Synthesis of Terminal and Internal Arylalkynes by the Palladium–Catalyzed Reaction of Alkynylzinc Reagents with Aryl Halides by Anthony O. King and Ei–ichi Negishi, *J. Org. Chem.* 43, No. 2, 1978 p. 358.

(List continued on next page.)

*Primary Examiner*—Paul J. Killos
*Attorney, Agent, or Firm*—Gabor L. Szekeres; Martin A. Voet; Robert J. Baran

[57] ABSTRACT

Compounds of the formula

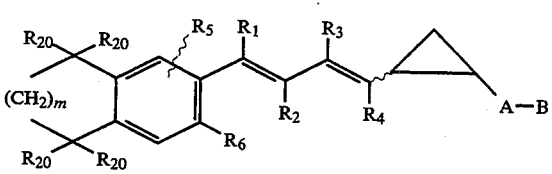

wherein m is 1–4; $R_1$–$R_4$ independently are hydrogen, lower alkyl of 1 to 6 carbons, Cl, Br, or I; $R_5$ is hydrogen, lower alkyl of 1 to 6 carbons, Cl, Br, I, lower alkoxy or lower thioalkoxy of 1–6 carbons; $R_6$ is hydrogen, lower alkyl, Cl, Br, I, $OR_{11}$, $SR_{11}$, $OCOR_{11}$, $SCOR_{11}$, $NH_2$, $NHR_{11}$, $N(R_{11})_2$, $NHCOR_{11}$ OR $NR_{11}$—$COR_{11}$; $R_{20}$ is independently hydrogen or lower alkyl; A is $(CH_2)_n$ where n is 0–5, lower branched chain alkyl having 3–6 carbons, cycloalkyl having 3–6 carbons, alkenyl having 2–6 carbons and 1 or 2 double bonds, alkynyl having 2–6 carbons and 1 or 2 triple bonds; B is hydrogen, COOH or a pharmaceutically acceptable salt thereof, $COOR_8$, $CONR_9R_{10}$, —$CH_2OH$, $CH_2OR_{11}$, $CH_2OCOR_{11}$, CHO, $CH(OR_{12})_2$, $CHOR_{13}O$, —$COR_7$, $CR_7(OR_{12})_2$, or $CR_7OR_{13}O$, where $R_7$ is an alkyl, cycloalkyl or alkenyl group containing 1 to 5 carbons, $R_8$ is an alkyl group of 1 to 10 carbons, or a cycloalkyl group of 5 to 10 carbons, or $R_8$ is phenyl or lower alkylphenyl, $R_9$ and $R_{10}$ independently are hydrogen, an alkyl group of 1 to 10 carbons, or a cycloalkyl group of 5–10 carbons, or phenyl or lower aklylphenyl, $R_{11}$ is lower alkyl, phenyl or lower alkylphenyl, $R_{12}$ is lower alkyl, and $R_{13}$ is divalent alkyl radical of 2–5 carbons, have retinoid-like activity.

25 Claims, 1 Drawing Sheet

U.S. PATENT DOCUMENTS

| | | | |
|---|---|---|---|
| 4,992,468 | 2/1991 | Chandraratna | 514/532 |
| 5,006,550 | 4/1991 | Chandraratna | 514/456 |
| 5,013,744 | 5/1991 | Chandraratna | 514/345 |
| 5,015,658 | 5/1991 | Chandraratna | 514/432 |
| 5,023,341 | 6/1991 | Chandraratna | 549/23 |
| 5,037,825 | 8/1991 | Klaus et al. | 514/233.8 |
| 5,045,551 | 9/1991 | Chandraratna | 514/337 |
| 5,053,523 | 10/1991 | Chandraratna | 549/398 |
| 5,068,252 | 11/1991 | Chandraratna | 514/543 |
| 5,089,509 | 2/1992 | Chandraratna | 514/337 |
| 5,130,335 | 7/1992 | Chandraratna | 514/510 |
| 5,134,159 | 7/1992 | Chandraratna | 514/456 |
| 5,162,546 | 11/1992 | Chandraratna | 549/23 |
| 5,175,185 | 12/1992 | Chandraratna | 514/445 |
| 5,183,827 | 2/1993 | Chandraratna | 514/444 |
| 5,202,471 | 4/1993 | Chandraratna | 562/473 |
| 5,231,113 | 7/1993 | Chandraratna | 514/510 |
| 5,234,926 | 8/1993 | Chandraratna | 514/253 |

OTHER PUBLICATIONS

Conversion of Methyl Ketones into Terminal Acetylenes and (E)-Tri-substituted Olefins of Terpenoid Origin by Ei-ichi, Anthony O. King, and William L. Klima, J. Org. Chem. 45, No. 12, 1980 p. 2526.

Sporn et. al. in J. Amer. Acad. Derm. 15:756-764 (1986).

A Convenient Synthesis of Ethynylarenes and Diethynlarenes by S. Takahashi, Y. Kuroyama, K. Sonogashira, N. Hagihara, Synthesis 1980 pp. 627-630.

Shudo et al. in Chem. Phar. Bull. 33:404-407 (1985).

Kagechika et. al. in J. Med. Chem. 31:2182-2192 (1988).

Chemistry and Biology of Synthetic Retinoids by Marcia I. Dawson and William H. Okamura, published by CRC Press Inc., 1990, pp. 334-335, 354.

Synthesis of 2,2'-Diacyl-1'-biaryls. Regiocontrolled Protection of... by Mervic, et al, J. Org. Chem., No. 45, pp. 4720-4725, 1980.

A Dopamine Receptor Model and Its Application in the Design of a New Class of Rigid Pyrrolo[2,3-g]isoquinoline Antipsychotics, Gary L. Olson, et al. American Chemical Society, 1981, vo. 24, No. 9, pp. 1026-1031.

6.2.3 Conformational Restriction, Williams, et al., Drug Discovery and Development, 1987 The Humana Press, pp. 54-55.

V. Retinoid Structure-Biological Activity Relationships, Chemistry and Biology of Synthetic Retinoids, pp. 324-356.

Davis et al. J. Organomettalic Chem 387 (1990) 381-390.

Effects of 13-Cis-Retinoic Acid, All-Trans-Retinoic Acid, and Acitretin on the Proliferation, Lipid Synthesis and Keratin Expression of Cultured Human Sebocytes In Vitro, C. C. Zouboulis, The Journal of Investigative Dermatology, vol. 96, No. 5, May 1991, pp. 792-797.

Organ maintenance of human sebaceous glands: in vitro effects of 13-cis retinoic acid and testosterone, John Ridden, et al., Journal of Cell Science, vol. 95, 1990, pp 125-136.

Characterization of Human Sebaceous Cells In Vitro, Thomas I. Doran, et al., The Journal of Investigative Dermatology, vol. 96, No. 3, Mar. 1991.

COMPOUND 6 (AGN 191758)

FIG. 1.

TETRAHYDRONAPHTHYL AND CYCLOPROPYL SUBSTITUTED 1,3-BUTADIENES HAVING RETINOID-LIKE ACTIVITY

BACKGROUND OF THE INVENTION

1. Field of the Invention

The present invention is directed to novel compounds which have retinoid-like biological activity. More specifically, the present invention relates to 1,3-butadiene compounds having a cyclopropane carboxylic acid substituent and a substituted tetrahydronaphthalene substituent. The acid function may also be converted to an alcohol, aldehyde or ketone, or derivatives thereof, or may be reduced to —$CH_3$.

2. Related Art

Compounds which have retinoid like activity are well known in the art, and are described in numerous United States and foreign patents and in scientific publications. It is generally known and accepted in the art that retinoid like activity is useful for treating animals of the mammalian species, including humans, for curing or alleviating the symptoms and conditions of numerous diseases and conditions. In other words, it is generally accepted in the art that pharmaceutical compositions having a retinoid like compound or compounds as the active ingredient are useful as regulators of cell proliferation and differentiation, and particularly as agents for treating dermatoses, such as acne, Darier's disease, psoriasis, icthyosis, eczema and atopic dermatitis, and for treating and preventing malignant hyperproliferative diseases such as epithelial cancer, breast cancer, prostatic cancer, head and neck cancer and myeloid leukemias, for reversing and preventing atherosclerosis and restenosis resulting from neointimal hyperproliferation, for treating and preventing other non-malignant hyperproliferative diseases such as endometrial hyperplasia, benign prostatic hypertrophy, proliferative vitreal retinopathy and dysplasias, for treating autoimmune diseases and immunological disorders (e.g. lupus erythematosus) for treating chronic inflammatory diseases such as pulmonary fibrosis, for treating and preventing diseases associated with lipid metabolism and transport such as dyslipidemias, for promoting wound healing, for treating dry eye syndrome and for reversing and preventing the effects of sun damage to skin.

Among the numerous prior art patents and publications pertaining to specific chemical compounds which have retinoid-like biological activity, the following are of special interest: In Journal of Organic Chemistry 1984, 49 1941–1944 Curley et al., describe cyclopropyl analogs of retinoic acid, and in Archives of Biochemistry and Biophysics Volume 238 May 1, 1985, pp 484 489 Cutler et al. disclose data on the biological activity of cyclopropyl analogs of retinoic acid. In Journal of Medicinal Chemistry 1991 Vol 34, 430–439 Spruce et al. describe 1-methyl,-1-(4,4-dimethylthiochroman-6-yl) 1,3-butadien-4-yl]cyclopropyl carboxylic acid (also known as 7-methyl-7-(4,4-dimethylthiochroman-6-yl)-2,3-methylene-6-heptadienoic acid).

SUMMARY OF INVENTION

The present invention relates to compounds of Formula 1 wherein m is 1-4;

$R_1$–$R_4$ independently are hydrogen, lower alkyl of 1 to 6 carbons, Cl, Br, or I;

$R_5$ is hydrogen, lower alkyl of 1 to 6 carbons, Cl, Br, I, lower alkoxy or lower thioalkoxy of 1-6 carbons;

$R_6$ is hydrogen, lower alkyl, Cl, Br, I, $OR_{11}$, $SR_{11}$, $OCOR_{11}$, $SCOR_{11}$, $NH_2$, $NHR_{11}$, $N(R_{11})_2$, $NHCOR_{11}$ OR $NR_{11}$—$COR_{11}$;

$R_{20}$ is independently hydrogen or lower alkyl;

A is $(CH_2)_n$ where n is 0–5, lower branched chain alkyl having 3–6 carbons, cycloalkyl having 3–6 carbons, alkenyl having 2–6 carbons and 1 or 2 double bonds, alkynyl having 2–6 carbons and 1 or 2 triple bonds;

B is hydrogen, COOH or a pharmaceutically acceptable salt thereof, $COOR_8$, $CONR_9R_{10}$, —$CH_2OH$, $CH_2OR_{11}$, $CH_2OCOR_{11}$, CHO, $CH(OR_{12})_2$, $CHOR_{13}O$, —$COR_7$, $CR_7(OR_{12})_2$, or $CR_7OR_{13}O$, where $R_7$ is an alkyl, cycloalkyl or alkenyl group containing 1 to 5 carbons, $R_8$ is an alkyl group of 1 to 10 carbons, or a cycloalkyl group of 5 to 10 carbons, or $R_8$ is phenyl or lower alkylphenyl, $R_9$ and $R_{10}$ independently are hydrogen, an alkyl group of 1 to 10 carbons, or a cycloalkyl group of 5–10 carbons, or phenyl or lower aklylphenyl, $R_{11}$ is lower alkyl, phenyl or lower alkylphenyl, $R_{12}$ is lower alkyl, and $R_{13}$ is divalent alkyl radical of 2–5 carbons.

In a second aspect, this invention relates to the use of the compounds of Formula 1 as regulators for cell proliferation and differentiation, and particularly as agents for treating dermatoses, such as ache, Darier's disease, psoriasis, icthyosis, eczema, atopic dermatitis, and for treating and preventing malignant hyperproliferative diseases such as epithelial cancer, breast cancer, prostatic cancer, head and neck cancer and myeloid leukemias, for reversing and preventing artherosclerosis and restenosis resulting from neointimal hyperproliferation, for treating and preventing other non-malignant hyperproliferative diseases such as endometrial hyperplasia, benign prostatic hypertrophy, proliferative vitreal retinopathy and dysplasias, for treating autoimmune diseases and immunological disorders (e.g. lupus erythematosus), for treating chronic inflammatory diseases such as pulmonary fibrosis, for treating and preventing diseases associated with lipid metabolism and transport such as dyslipidemias, for promoting wound healing, for treating dry eye syndrome and in reversing and preventing the effects of sun damage to skin This invention also relates to a pharmaceutical composition comprising a compound of Formula 1 in admixture with a pharmaceutically acceptable excipient.

In another aspect, this invention relates to the process for making a compound of Formula 1, which process comprises reacting a compound of Formula 2 with a compound of Formula 3.

Formula 2

Formula 3 where the symbols are defined as above in connection with Formula 1; converting the ester of Formula 1 to an acid; and to prepare compounds in which A is $(CH_2)_n$ and n is 1-5, homologating a compound of Formula 1 to increase the value of n, or converting an acid of Formula 1 to an ester; or converting an acid of Formula 1 to an amide; or reducing and acid of Formula 1 to an alcohol of aldehyde; or converting an alcohol of Formula 1 to an ether or ester; or converting an aldehyde of Formula 1 to an acetal.

DETAILED DESCRIPTION OF THE INVENTION

General Embodiments

Definitions

The term alkyl refers to and covers any and all groups which are known as normal alkyl, branched-chain alkyl and cycloalkyl. The term alkenyl refers to and covers nominal alkenyl, branch chain alkenyl and cycloalkenyl groups having one or more sites of unsaturation. Lower alkyl means the above-defined broad definition of alkyl groups having 1 to 6 carbons, and as applicable, 3 to 6 carbons for branch chained and cycloalkyl groups. Lower alkenyl is defined similarly having 2 to 6 carbons for normal alkenyl, and 3 to 6 carbons for branch chained and cycloalkenyl groups.

The term "ester" as used here refers to and covers any compound falling within the definition of that term as classically used in organic chemistry. It includes organic and inorganic esters. Where B (of Formula 1) is —COOH, this term covers the products derived from treatment of this function with alcohols or thioalcohols preferably with aliphatic alcohols having 1-6 carbons. Where the ester is derived from compounds where B is —CH$_2$OH, this term covers compounds derived from organic acids capable of forming esters including phosphorous based and sulfur based acids, or compounds of the formula —CH$_2$OCOR$_{11}$ where R$_{11}$ is defined as above.

Amides has the meaning classically accorded that term in organic chemistry. In this instance it includes the unsubstituted amides and all aliphatic and aromatic mono- and di- substituted amides.

A pharmaceutically acceptable salt may be prepared for any compounds in this invention having a functionality capable of forming such-salt, for example an acid functionality. A pharmaceutically acceptable salt is any salt which retains the activity of the parent compound and does not impart any deleterious or untoward effect on the subject to which it is administered and in the context in which it is administered.

Pharmaceutically acceptable salts may be derived from organic or inorganic bases. The salt may be a mono or polyvalent ion. Of particular interest are the inorganic ions, sodium, potassium, calcium, and magnesium. Organic salts may be made with amines, particularly ammonium salts such as mono-, di- and trialkyl amines or ethanol amines. Salts may also be formed with caffeine, tromethamine and similar molecules. Where there is a nitrogen sufficiently basic as to be capable of forming acid addition salts, such may be formed with any inorganic or organic acids or alkylating agent such as methyl iodide. Preferred salts are those formed with inorganic acids such as hydrochloric acid, sulfuric acid or phosphoric acid. Any of a number of simple organic acids such as mono-, di- or tri- acid may also be used.

The compounds of the present invention contain at least two double bonds and therefore may have trans and cis (E and Z) isomers. In addition, some of the compounds used in the method of treatment of the present invention may contain one or more chiral centers and therefore exist in enantiomeric and diastereomeric forms. The scope of the present invention is intended to cover all such isomers per se, as well as mixtures of cis and trans isomers, mixtures of diastereomers and racemic mixtures of enantiomers (optical isomers) as well.

The preferred compounds of this invention are those of Formula 1 where A is $(CH_2)_n$ and n is 0,1, or 2; and B is —COOH, an alkali metal salt or organic amine salt thereof. Alternatively, compounds are preferred where B is represented by COOR$_8$ (ester) where R$_8$ is lower alkyl, CONR$_9$R$_{10}$ where R$_9$ and R$_{10}$ are hydrogen or lower alkyl (amide), CH$_2$OH (alcohol), CH$_2$OCOR$_{11}$, CH$_2$OR$_{11}$ where R$_{11}$ is lower alkyl; (lower alkyl esters and ethers formed with lower alkanol) or B is —CHO or CH(OR$_{12}$)$_2$, CHOR$_{13}$O (acetal derivatives), where R$_{12}$ and R$_{13}$ are defined as in connection with Formula 1.

With regard to m in the preferred compounds of the invention m is 2 (tetrahydronaphthalene derivatives) or m is 1 (indane) derivatives.

With respect to the symbols R$_2$, R$_3$, R$_4$, in Formula 1 and 2, R$_2$–R$_4$ are preferably hydrogen or lower alkyl, more preferably hydrogen. The substituent R$_1$ is preferably hydrogen or lower alkyl, more preferably, lower alkyl, most preferably methyl. Similarly R$_6$ is preferably hydrogen or lower alkyl. The R$_5$ substituent is preferably hydrogen or lower alkyl, more preferably hydrogen. In the most preferred compounds the double bonds of the 1-3 butadiene portion are always trans, trans or (E,E).

Particularly preferred compounds are with reference to Formula 4:

Formula 4

Ethyl cis-2-[4-methyl-4-(5,5,8,8,-tetramethyl-5,6,7,8-tetrahydro-2-naphthyl)-(E),(E) 1-3-butadienyl]-1-cyclopropane carboxylate, Compound 1; R$_6$ is H, R$_8$ is ethyl, and the configuration is cis about the cyclopropyl ring;

Ethyl trans-2-[4-methyl-4-(5,5,8,-tetramethyl-5,6,7,8-tetrahydro-2-naphthyl)-(E),(E) 1 3-butadienyl]-1-cyclopropane carboxylate, compound 2; $R_6$ is H, $R_8$ is ethyl, and the configuration is trans about the cyclopropyl ring;

Trans-2-[4-methyl-4-(5,5,8,8,-tetramethyl-5,6,7,8-tetrahydro-2-naphthyl)-(E),(E) 1-3-butadienyl]-1-cyclopropane carboxylic acid, Compound 3; $R_6$ is H, $R_8$ is H, and the configuration is trans about the cyclopropyl ring;

Cis-2-[4-methyl-4-(5,5,8,8,-tetramethyl-5,6,7,8-tetrahydro-2-naphthyl)-(E),(E) 1-3-butadienyl]-1-cyclopropane carboxylic acid, Compound 4; $R_6$ is H, $R_8$ is H, and the configuration is trans about the cyclopropyl ring;

Ethyl cis-2-[4-methyl-4-(3,5,5,8,8,-pentamethyl-5,6,7,8-tetrahydro-2-naphthyl)-(E),(E) 1-3-butadienyl]-1-cyclopropane carboxylate, Compound 5; $R_6$ is $CH_3$, $R_8$ is ethyl, and the configuration is cis about the cyclopropyl ring;

Cis-2-[4-methyl-4-(3,5,5,8,8,-pentamethyl-5,6,7,8-tetrahydro-2-naphthyl)-(E),(E) 1-3-butadienyl]-1-cyclopropane carboxylic acid, Compound 6; $R_6$ is $CH_3$, $R_8$ is H, and the configuration is cis about the cyclopropyl ring;

Ethyl trans-2-[4-methyl-4-(3,5,5,8,8,-pentamethyl-5,6,7,8-tetrahydro-2-naphthyl)-(E),(E) 1-3-butadienyl]-1-cyclopropane carboxylate, Compound 7; $R_6$ is CH3, $R_8$ is ethyl, and the configuration is trans about the cyclopropyl ring;

Trans-2-[4-methyl-4-(3,5,5,8,8,-pentamethyl-5,6,7,8-tetrahydro-2-naphthyl)-(E),(E) 1-3-butadienyl]-1-cyclopropane carboxylic acid, Compound 8; $R_6$ is CH3, $R_8$ is H, and the configuration is trans about the cyclopropyl ring.

The compounds of this invention may be administered systemically or topically, depending on such considerations as the condition to be treated, need for site-specific treatment, quantity of drug to be administered, and numerous other considerations.

In the treatment of dermatoses, it will generally be preferred to administer the drug topically, though in certain cases such as treatment of severe cystic ache or psoriasis, oral administration may also be used. Any common topical formulation such as a solution, suspension, gel, ointment, or salve and the like may be used. Preparation of such topical formulations are well described in the art of pharmaceutical formulations as exemplified, for example, Remington's Pharmaceutical Science, Edition 17, Mack Publishing Company, Easton, Pa. For topical application, these compounds could also be administered as a powder or spray, particularly in aerosol form. If the drug is to be administered systemically, it may be confected as a powder, pill, tablet or the like or as a syrup or elixir suitable for oral administration. For intravenous or intraperitoneal administration, the compound will be prepared as a solution or suspension capable of being administered by injection. In certain cases, it may be useful to formulate these by injection. In certain cases, it may be useful to formulate these compounds in suppository form or as extended release formulation for deposit under the skin or intramuscular injection.

Other medicaments can be added to such topical formulation for such secondary purposes as treating skin dryness; providing protection against light; other medications for treating dermatoses; medicaments for preventing infection, reducing irritation, inflammation and the like.

Treatment of dermatoses or any other indications known or discovered to be susceptible to treatment by retinoid-like compounds will be effected by administration of the therapeutically effective dose of one or more compounds of the instant invention. A therapeutic concentration will be that concentration which effects reduction of the particular condition, or retards it expansion. In certain instances, the compound potentially may be used in prophylactic manner to prevent onset of a particular condition. A useful therapeutic or prophylactic concentration will vary from condition to condition and in certain instances may vary with the severity of the condition being treated and the patient's susceptibility to treatment. Accordingly, no single concentration will be uniformly useful, but will require modification depending on the particularities of the disease being treated. Such concentrations can be arrived at through routine experimentation. However, it is anticipated that in the treatment of, for example, acne, or similar dermatoses, that a formulation containing between 0.01 and 1.0 milligrams per milliliter of formulation will constitute a therapeutically effective concentration for total application. If administered systemically, an amount between 0.01 and 5 mg per kg per day of body weight would be expected to effect a therapeutic result in the treatment of many disease for which these compounds are useful.

The retinoid-like activity of these compounds is confirmed through the classic measure of retinoic acid activity involving the effects of retinoic acid on ornithine decarboxylase. The original work on the correlation-between retinoic acid and decrease in cell proliferation was done by Verma & Boutwell, Cancer Research, 1977, 37,2196–2201. That reference discloses that ornithine decarboxylase (ODC) activity increased precedent to polyamine biosynthesis. It has been established elsewhere that increases in polyamine synthesis can be correlated or associated with cellular proliferation. Thus, if ODC activity could be inhibited, cell hyperproliferation could be modulated. Although all causes for ODC activity increases are unknown, it is known that 12-0-tetradecanoylphorbol-13-acetate (TPA) induces ODC activity. Retinoic acid inhibits this induction of ODC activity by TPA. An assay essentially following the procedure set out in Cancer Res: 1662–1670,1975 may be used to demonstrate inhibition of TPA induction of ODC by compounds of this invention. The results of this assay for certain examplary compounds of the invention are shown in Table 1 below.

| Compound # | $IC_{80}$ (nmol) |
| --- | --- |
| 1 | 8.3 |
| 2 | 2.1 |
| 3 | 2.6 |
| 4 | 35 |
| 5 | >300 |
| 6 | 638 |
| 7 | 250 |

Another assay in which retinoid like activity of the compounds used in accordance with the invention are confirmed is the HL-60 transglutaminase induction, the procedures of which are described as follows:
TISSUE TRANSGLUTAMINASE ASSAY (tTGASE) IN HL-60 CELLS HL-60 cells were grown as a suspension culture in T-162 $cm^2$ flasks in serum-free RPMI 1640 medium supplemented with insulin (5 $\mu$g/ml), transferrin (5 $\mu$g/ml), and selenium (3 nM). The cells ($1 \times 10^6$ cells/well, in 6-well dishes) were treated with serial dilutions of test compounds in the above RPMI 1640 medium which was additionally supplemented with 1 nM dibutyryl cyclic adenosine monophosphate, a component found to be necessary for efficient differentiation of the cells. Ethanol was used in the vehicle control cultures. After 1 days of incubation at 37° C. in a 7.5% $CO_2$ incubator, the cells were collected in a set of tubes and pelleted by centrifugation. The cells were lyzed in a buffer containing 20 mM Tris-HCl, pH 7.5, 1 mM EDTA, and 0.5% Triton X-100. An aliquot of the cell lysate was assayed for tTGASE activity in a reaction mixture containing 20 mM Tris-HCl, pH 7.5, 5 mM $CaCl_2$, 2 mg/ml dimethylcasein, 15 mM B-mercaptoethanol and 50 $\mu$Ci/ml [2,3-$^3$H] putrescine dihydrochloride. The reaction was carried out for 60 minutes in a 37° C. shaking water bath. The reaction was stopped by an addition of 10% trichloroacetic acid containing 0.1% putrescein. An aliquot of the stopped reaction mixture was spotted on Whatman 3 MM filter discs. The filter discs, along with the control blank filter discs, were washed twice with 5% trichloroacetic acid containing 0.1% putrescein and twice with methanol. After drying under a heat lamp, the radioactivity in the filter discs was determined by scintillation counting. An aliquot of the cell lysates was also assayed for protection concentration by the Bradford method (Bio-Rad). After subtracting the radioactivity from the control blank filter discs, the data were calculated and expressed as pmol/min/mg protein.

Figure 1:
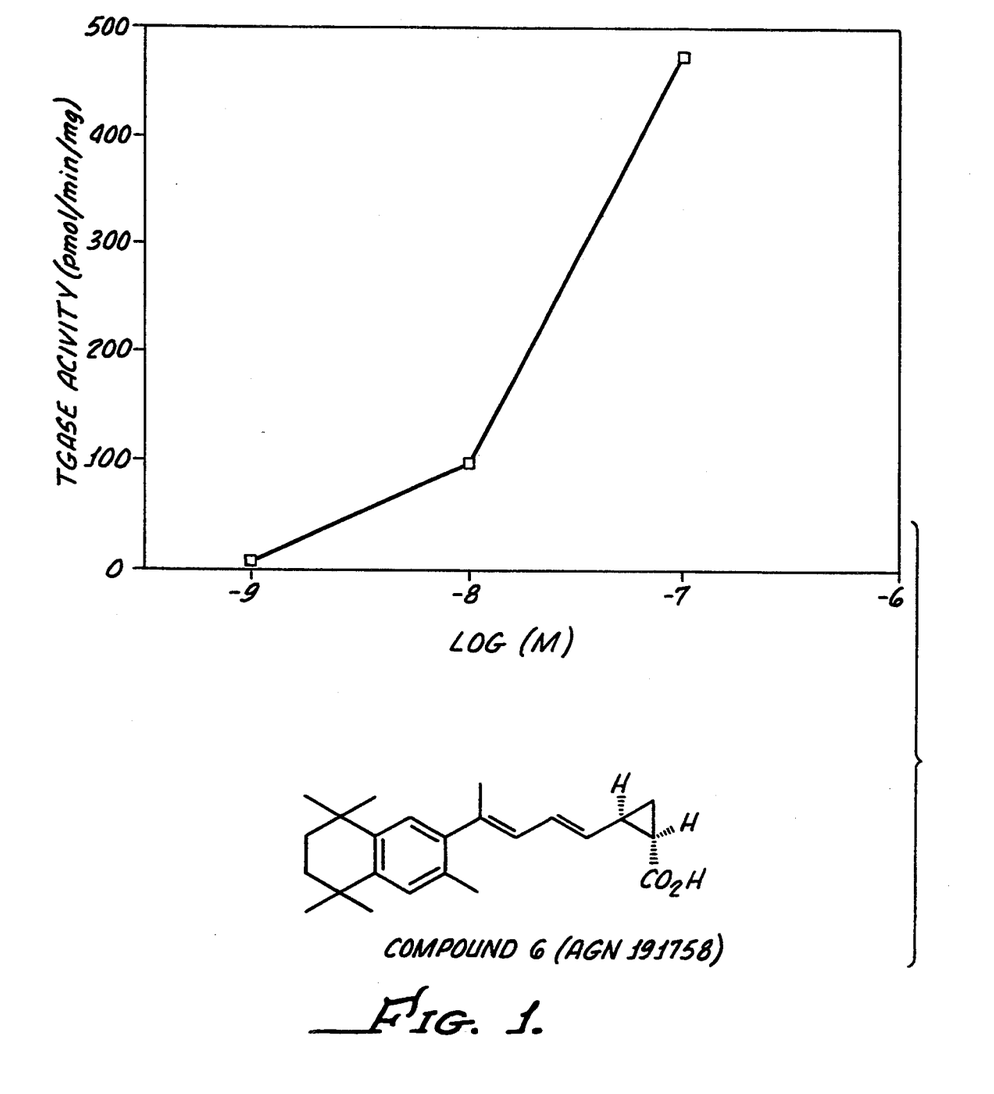
FIG. 1 is a graph showing the results of a Tissue Transglutaminase Assay in HL-60 cells, with Compound 6 (AGN 191758) of the present invention.

As is well understood in the art, induction of tranglutaminase activity in the just-described assay is an early marker of retinoid like activity. The graph of FIG. 1 shows the results of this test for Compound 6 of this invention. This compound is also designated AGN 191758.

Synthetic Processes for Preparing Compounds of the Invention

It is anticipated that the compounds of this invention can be made by a number of different synthetic chemical pathways. To illustrate this invention, there is here laid out a series of steps which will provide the compounds of Formula 1 where m is 2, (tetrahydronaphthalene derivatives) when such synthesis is followed in tone and in spirit. The synthetic chemist will readily appreciate that the conditions set out here are specific embodiments which can be generalized to any and all of the compounds represented by Formula 1. Specifically, in order to prepare the compounds of the invention where m is 1, 3, or 4 the sequence of reactions outlined in Reaction Scheme 1 is followed, but the sequence is started with a compound which is the indane, cycloheptanobenzene or cyclooctanobenze analog of Formula 5.

Reaction Scheme 1 shows a synthetic route to the compounds of the invention. A 5,5,7,8-tetrahydro-napthalene compound of Formula 5, which has the desired $R_5$, $R_6$, and $R_{20}$ substitutents (as defined in connection with Formula 1) is reacted under Friedel Crafts like conditions with a reagent such as $R_1COCl$ ($R_1$ is defined in connection with Formula 1) to introduce the $R_1$-CO ketone function into the 2-position of the naphthalene nucleus. When $R_1$ is methyl then the reagent in the Friedel Crafts type reaction is typically acetyl chloride. The ketone of Formula 6 is reacted with vinyl magnesium bromide to give the tertiary alcohol of Formula 7.

The alcohol of Formula 7 is reacted with triphenylphosphine hydrobromide. This reaction results in migration of the double bond and formation of the triphenylphosphonium salt of Formula 8 where the triphenylphosphonium moiety is attached to a primary carbon. The double bond obtained in this process is usually predominantly of trans (E) configuration. The triphenylphosphonium salt of Formula 8 is a Wittig reagent, which is reacted with the cyclopropane aldehyde derivative of Formula 9 to provide the diene compound of Formula 10. This reaction is typically conducted in the presence of a base, such as 1,2-epoxybutane. The double bond formed in the last mentioned reaction is a mixture of cis (Z) and trans (E) isomers, but the ratio of the trans (E) isomer can be increased by isomerization with iodine. The cis and trans isomers can usually be separated by appropriate techniques such as high pressure liquid chromatography (HPLC).

The Wittig reaction between the triphenylphosphonium salt of Formula 8 and the aldehyde of Formula 9 can also be conducted in the presence of n-BuLi or other appropriate bases.

The compound of Formula 10 which is formed as a result of the Wittig reaction has the essential structural features of the compounds used in accordance with the present invention. Thus, the compound of Formula 10 may be the target compound made in accordance with the invention, (in this case Formula 10 depicts compounds of Formula 1) or maybe readily converted into the target compound by such steps as salt formation, esterification, deesterification, homologation, amide formation and the like. These steps are further discussed below.

Specifically, the compounds of Formula 10 may be subjected to further transformations, particularly as far as synthetic transformation of the $COOR_8$ group is concerned. As far as the synthesis of compounds analogous to the compounds of Formula 10, but differring therefrom in the functionality of the A-B group (see for example Formula 1) is concerned, (and by extension of the principles to any and all compounds used in accordance with the invention) the following further well known and published general principles and synthetic methodology are noted.

Carboxylic acids are typically esterified by refluxing the acid in a solution of the appropriate alcohol in the presence of an acid catalyst such as hydrogen chloride or thionyl chloride. Alternatively, the carboxylic acid can be condensed with the appropriate alcohol in the presence of dicyclohexylcarbodiimide and dimethylaminopyridine. The ester is recovered and purified by conventional means. Acetals and ketals are readily made by the method described in March, "Advanced Organic Chemistry," 2nd Edition, McGraw-Hill Book Company, p 810). Alcohols, aldehydes and ketones all may be protected by forming respectively, ethers and esters, acetals or ketals by known methods such as those described in McOmie, Plenum Publishing Press, 1973 and *Protecting Groups*, Ed. Greene, John Wiley & Sons, 1981.

A means for making compounds where A is $(CH_2)_n$ (n is 1–5) is to subject the compounds of Formula 1, (or of Formula 10) where B is an acid or other function, to homologation, using the well known Arndt-Eistert method of homologation, or other known homologation procedures.

Compounds of Formula 1, where A is an alkenyl group having one or more double bonds can be made for example, by having the requisite number of double bonds incorporated into the cyclopropane derivative intermediate which is coupled as an aldehyde with the triphenylphosphonium salt of Formula 8. Generally speaking, such compounds where A is an unsaturated carbon chain can be obtained by synthetic schemes well known to the practicing organic chemist; for example by Wittig and like reactions, or by introduction of a double bond by elimination of halogen from an alpha-halo-carboxylic acid, ester or like carboxaldehyde. Compounds of Formula 1 where the A group has a triple (acetylenic) bond can be made by using the corresponding cyclopropane aldehyde intermediate. Such intermediate can be obtained by reactions well known in the art, for example, by reaction of a corresponding methyl ketone with strong base, such as lithium diisopropyl amide.

The acids and salts derived from compounds of Formula 1 and of Formula 10 are readily obtainable from the corresponding esters. Basic saponification with an alkali metal base will provide the acid. For example, an ester of Formula 1 or of Formula 10 may be dissolved in a polar solvent such as an alkanol, preferably under an inert atmosphere at room temperature, with about a three molar excess of base, for example, potassium hydroxide. The solution is stirred for an extended period of time, between 15 and 20 hours, cooled, acidified and the hydrolysate recovered by conventional means.

The amide may be formed by any appropriate amidation means known in the art from the corresponding esters or carboxylic acids. One way to prepare such compounds is to convert an acid to an acid chloride and then treat that compound with ammonium hydroxide or an appropriate amine. For example, the acid is treated with an alcoholic base solution such as ethanolic KOH (in approximately a 10% molar excess) at room temperature for about 30 minutes. The solvent is removed and the residue taken up in an organic solvent such as diethyl ether, treated with a dialkyl formamide and then a 10-fold excess of oxalyl chloride. This is all effected at a moderately reduced temperature between about $-10$ degrees and $+10$ degrees C. The last mentioned solution is then stirred at the reduced temperature for 1–4 hours, preferably 2 hours. Solvent removal provides a residue which is taken up in an inert organic solvent such as benzene, cooled to about 0 degrees C. and treated with concentrated ammonium hydroxide. The resulting mixture is stirred at a reduced temperature for 1–4 hours. The product is recovered by conventional means.

Alcohols are made by converting the corresponding acids to the acid chloride with thionyl chloride or other means (J. March, "Advanced Organic Chemistry", 2nd Edition, McGraw-Hill Book Company), then reducing the acid chloride with sodium borohydride (March, Ibid, pg. 1124), which gives the corresponding alcohols. Alternatively, esters may be reduced with lithium aluminum hydride at reduced temperatures. Alkylating these alcohols with appropriate alky halides under Williamson reaction conditions (March, Ibid, pg. 357) gives the corresponding ethers. These alcohols can be converted to esters by reacting them with appropriate acids in the presence of acid catalysts or dicyclohexylcarbodiimide and dimethlaminopyridine.

Aldehydes can be prepared from the corresponding primary alcohols using mild oxidizing agents such as pyridinium dichromate in methylene chloride (Corey, E. J., Schmidt, G., *Tet. Lett.*, 399, 1979), or dimethyl sulfoxide/oxalyl chloride in methylene chloride (Omura, K., Swern, D., *Tetrahedron*, 1978, 34, 1651).

Ketones can be prepared from an appropriate aldehyde by treating the aldehyde with an alkyl Grignard reagent or similar reagent followed by oxidation.

Acetals or ketals can be prepared from the corresponding aldehyde or ketone by the method described in March, Ibid, p 810.

Specific Examples

1-[8,8-dimethyl (5,6,7,8-tetrahydronaphthalen)-2-yl] ethanol and 1-[8,8-dimethyl (5,6,7,8-tetrahydronaphthalen)-3-yl] ethanol To a stirred solution of 4.27 g (32.0 mmol) of anhydrous aluminum chloride in 15 ml of methylene chloride at 0° C. was added a solution of 4.0 g (25.0 mmol) of 1,1-dimethyltetralin (Davidson et al. J. Amer. Chem. Soc. 1934, 56 p 962) and 2.35 g (30.0 mmol) of acetyl chloride in 5 ml of methylene chloride. The mixture was allowed to warm to room temperature over a period of one hour and then treated with 70 ml of ice water. The organic layer was isolated and washed with 20 ml of dilute HCl, 40 ml of water, and 40 ml of brine and dried (MgSO4). Solvent was removed in-vacuo and the residue was purified using fractional distillation (97–99 C., 0.1 mm). The resulting methyl [8,8-dimethyl (5,6,7,8-tetrahydronaphthalen)-2-yl] ketone and methyl [8,8-dimethyl (5,6,7,8-tetrahydronaphthalen)-3-yl] ketone isomers were separable only after reduction to the corresponding alcohols. To this end, lithium aluminum hydride (0.250 g, 6.7 mmol) in 30 ml of dry ether was added dropwise to a solution of 4.0 g (19.8 mmol) of methyl [8,8-dimethyl (5,6,7,8-tetrahydronaphthalen)-2-yl] ketone and methyl [8,8-dimethyl (5,6,7,8-tetrahydronaphthalen)-3-yl] ketone in 10 ml of anhydrous ether. The mixture was refluxed gently for 30 minutes and treated with ethyl acetate, water, and dilute hydrochloric acid. The organic layer was washed with water, brine and dried (MgSO4). Solvent was removed in-vacuo and the resulting isomeric mixture was purified and separated, using HPLC (Whatman M20 partisil, 10% ethyl acetate in hexanes at 9.9 ml per minute) to give the title compounds as colorless oils: 1-[8,8-dimethyl (5,6,7,8-tetrahydronaphthalen)-2-yl] ethanol, PMR(CDCl$_3$): δ1.28 (6H, s), 1.47 (3H, d, J~6.7 Hz), 1.65 (2H, m), 1.78 (2H, m), 2.74 (2H, t, J~6.3 Hz), 4.82(1H, q, J~6.7 Hz), 7.02 (1H,d,J~7.8 Hz), 7.08 (1H, dd, J~1.8 Hz, J~7.8 Hz), 7.32 (1H, d, J~1.8 Hz), and 1 [8,8-dimethyl (5,6,7,8-tetrahydronaphthalen)-3-yl] ethanol PMR (CDCl$_3$): δ1.27(6H,s),147(3H,d,J~6.7 Hz), 1.65(2H,m), 1.78(2H,m), 2.74(2H,t,J~6.3 Hz), 4.78(1H,q,J~6.7 Hz),7.02(1H,d,J~1.8 Hz), 7.11(1H,dd,J~8.1 Hz, J~1.8 Hz), 7.2(1H,d,J~8.1 Hz)

Methyl [8,8 dimethyl (5,6,7,8-tetrahydronaphthalen)-2yl-] ketone

To a stirred solution of 2.44 g (11.96 mmol) of 1-[8,8-dimethyl (5,6,7,8-tetrahydrodnapthalen)-2-yl] ethanol in 35 ml of methylene chloride was added 6.75 g (17.9 mmol) of pyridinium dichromate and 0.33 g (1.68 mmol) of pyridinium trifluroacetate at room temperature. The mixture was stirred for 16 hours and diluted with an equal volume of petroleum ether which caused a precipitate. The suspension was filtered through anhydrous MgSO$_4$ and silica gel (6 mm). Solvent was removed in-vacuo to give the title compound as a colorless liquid. PMR(CDCl$_3$): δ1.3 (6H,s), 1.67 (2H,m), 1.8 (2H,m), 2.55 (3H,s), 2.78 (2H,m), 7.08 (1H, d, J~8.0 Hz), 7.60 (1H, dd, J~8.0 Hz, J~1.8 Hz), 7.93 (1H, d, J~1.8 Hz).

Methyl [3,5,5,8,8-pentamethyl(5,6,7,8-tetrahydronaphthalen)-2-yl] ketone (Compound 20)

To a suspension of 6.71 g (50.3 mmol) of aluminum chloride in methylene chloride at 0 ° C. under argon was added a solution of 3.95 g (3.58 mL, 50.3 mmol) of acetyl chloride and 10.21 g (41.9 mmol) of 3,5,5,8,8-pentamethyl-5,6,7,8-tetrahydronaphthalene in methylene chloride. The resulting mixture was allowed to warm to room temperature over a period of 3 hours with stirring. The mixture was recooled to 0° C. and 1N HCl was dropwise added. The mixture was then taken-up in water and extracted three times with methylene chloride. The organic layers were washed with 1N HCl, water, brine, and dried (MgSO4). Solvent was removed in-vacuo and the resulting residue purified using flash chromatography to give the title compound as an ivory solid.

PMR (CDCl$_3$): δ1.28 (6H, s), 1.30 (6H, s), 1.69 (4H, s), 2.49 (3H, s), 2.57 (3H, s), 7.15 (1H, s), 7.67 (1H, s).

2-[3,5,5,8,8,-pentamethyl-5,6,7,8-tetrahydronapthalen)-2-yl]-but-3-en-2-ol (Compound 21)

To a stirred solution of 5.36 g (21.9 mmol) of methyl [3,5,5,8,8,-pentamethyl (5,6,7,8-tetrahydronapthalen)-2-yl] ketone (Compound 20) dissolved in 38 ml of freshly distilled tetrahydrofuran at 0° C. under argon was added 37.4 ml of 1.0M solution of vinyl magnesium bromide in tetrahydrofuran dropwise via syringe. The resulting mixture was allowed to warm to room temperature over a period of 2 hours with stirring. The mixture was recooled to 0° C. and saturated aqueous ammonium chloride solution was added dropwise. The mixture was then extracted with ether and the ether layers were washed with water, saturated sodium bicarbonate, brine, and dried (MgSO4). The solvent was removed in-vacuo and the residue purified using flash chromatography (SiO$_2$, 3% ethyl acetate in hexanes) to give the title compound as a white solid.

PMR (CDCl$_3$): δ1.26(6H,s), 1.27 (6H,s), 1.66 (4H,s), 1.70(3H,s), 2.40 (3H,s), 5.14 (1H, dd, J~11 Hz, J~1.2 Hz), 5.23 (1H, dd, J~17 Hz, J~1.2 Hz), 6.16 (1H, dd, J~11 Hz, J~17 Hz), 7.04 (1H,s), 7.40 (1H,s).

Triphenyl [3-(5,6,7,8-tetrahydro-3,5,5,8,8,-pentamethyl-2-naphthalenyl)-2-buten-yl] phosphonium bromide (E) (Compound 22)

To a solution of 6.30 g (18.4 mmol) triphenylphosphonium hydrobromide in 50 ml of methanol was added 5.02 g (18.4 mmol) of 2-[3,5,5,8,8,-pentamethyl-5,6,7,8-tetrahydronapthalen)-2-yl]-but-3-en-2-ol (Compound 21) in 50 ml of methanol via addition funnel dropwise at room temperature under argon. The solvent was removed in-vacuo after 16 hours of stirring and the residue was purified using flash chormatography (SiO$_2$, 5% methanol in methylene chloride) to give the title compound as a white foam.

PMR(CDCl$_3$): δ1.21(6H,s),1.23(6H,s),1.63(4H,s), 1.80(3H,d,J~6 Hz), 2.06(3H,m), 4.84(2H,m), 5.31(1H,s), 6.78(1H,s), 7.0(1H,s), 7.65–7.97(15H,m).

2,5-Dichloro-2,5-dimethylhexane

Hydrogen chloride gas was bubbled through a suspension of 48 g (0.33 mol) of 2,5-dimethyl-2,5-hexanediol in 600 ml conc. hydrogen chloride until the solution was saturated. The resulting crystalline produce was collected by filtration, washed repeatedly with water and dried on a vacuum line to give the title compound as a crystalline white solid. PMR (CDCl$_3$): $\delta$1.60 (12H, s), 1.94 (4H, s).

5,5,8,8-Tetramethyl-5,6,7,8-tetrahydronaphthalene

A vigorously stirred solution of 100 g (0.55 mol) of 2,5-dichloro-2,5-dimethylhexane in 300 ml benzene was cooled in an ice bath and treated with 45 g (0.34 mol) of anhydrous aluminum chloride in small portions. This mixture was stirred at room temperature for 3 hours, refluxed for 1 hour, cooled and poured into a mixture of ice and hydrogen chloride. The organic layer was recovered and the aqueous layer extracted with ether. Organic extracts were combined, washed with water, saturated Na$_2$CO$_3$ and saturated NaCl solutions and dried (MgSO$_4$).

After removing the solvent, the residue was fractionally distilled (78° C., 0.8 mm) to give the title compound as a colorless liquid. PMR (CDCl$_3$): $\delta$1.3 (12H, s), 1.7 (4H, s), 7.1 (2H, m), 7.5 (2H, m).

Methyl [5,5,8,8-tetramethyl(5,6,7,8-tetrahydronaphthalen)-2-yl] ketone (Compound 23)

A suspension of 3.45 g (25.9 mmol) aluminum chloride in 15 ml methylene chloride was cooled under argon in an ice/salt bath and treated while stirring with a mixture of 4 g(21.2 mmol) 5,5,8,8-tetramethyl-5,6,7,8-tetrahydro naphthalene and 1.94 g (24.7 mmol) acetyl chloride via a dropping funnel over a period of 0.5 hours. Then the cooling bath was removed, the mixture stirred for 2 hours at room temperature and the reaction quenched with ice. The organic layer was recovered and the aqueous layer extracted with 2×50 ml methylene chloride.

The organic extracts were combined and washed with water, saturated NaHCO$_3$ solution and dried (MgSO$_4$). Solvent was removed in vacuo and the residue kugelrohr distilled (90° C.; 0.45 mm) to give the title compound as a colorless oil. PMR (CDCl$_3$): $\delta$1.32 (6H, s), 1.33 (6H, s), 1.72 (4H, s), 2.60 (3H, s), 7.41 (1H, d, J$\sim$8.8 Hz), 7.71 (1H, dd, J$\sim$8.8, 2.6 Hz), 7.96 (1H, d, J$\sim$2.6 Hz).

2-[5,5,8,8-tetramethyl-(5,6,7,8-tetrahydronaphthalen)-2-yl]-2-but-3-enol (Compound 24)

To a stirred solution of 5.0 g (21.6 mmol) of freshly distilled (5,5,8,8,-tetramethyl (5,6,7,8,-tetrahydronaphthalen)-2-yl] ketone (Compound 23) in 30 ml of tetrahydrofuran was added dropwise 43 ml (43.2 mmol) of vinyl magnesium bromide at 0° C. under argon. The solution was allowed to come to room temperature over a period of 72 hours with stirring. The mixture was quenched with saturated aqueous ammonium choride and extracted with ether. The ether layers were washed with water, brine, and dried (MgSO4). The solvent was removed in-vacuo and the residue purified using flash chromatography (SiO2, 5% ethyl acetate in hexanes) to give the title compound as a yellow oil.

PMR (CDCl$_3$): $\delta$1.28 (6H,s), 1.30 (6H,s), 1.64 (3H,s), 1.68 (3H,s), 1.84 (1H,s), 5.32 (1H,d, J$\sim$17 Hz), 5.13 (1H,d, J$\sim$10 Hz), 6.18 (1H, dd, J$\sim$17 Hz, J$\sim$10 Hz), 7.2 (1H, dd J$\sim$2 Hz, J$\sim$8 Hz), 7.28 (1H,d,J$\sim$8 Hz), 7.4 (1H, d, J$\sim$2 Hz).

Triphenyl[3-(5,6,7,8-tetrahydro-5,5,8,8-tetramethyl-2-naphthalenyl)-2-butenyl-phosphonium bromide, (E) (Compound 25)

To a solution of 3.23 g (9.44 mmol) of triphenylphosphine hydrobromide in 30 ml of methanol was added 2.45 g (9.44 mmol) of 2-[5,5,8,8-tetramethyl-(5,6,7,8-tetrahydtronapthalen)-2-yl]-2-but-3-enol., (Compound 24) in 30 ml of methanol, dropwise at room temperature. The solvent was removed in-vacuo after 16 hours of stirring and the residue purified using flash chromatography (SiO$_2$, 5% methanol in methylene chloride) to give the title compound as an off-white solid.

PMR (CDCl$_3$): $\delta$1.23(6H,s), 1.25(6H,s), 1.64(3H,s), 1.65(4H,s), 4.88(2H,dd,J$\sim$15 Hz, J$\sim$8.0 Hz), 5.54–5.62(1H,m), 6.93(1H,dd,J$\sim$8 Hz, J$\sim$2 Hz), 7.07(1H,d,J$\sim$2 Hz), 7.20(1H,d,J$\sim$8 Hz), 7.66–7.95(15H,m)

Ethyl cis-2-[4-methyl-4(5,6,7,8-tetrahyro-5,5,8,8-tetramethyl-2-naphthyl) E,E 1-3 butadienyl] 1-cyclopropane carboxylate (Compound 1)

A suspension of 1.67 g (2.5 mmol) of triphenyl[3-(5,6,7,8-tetrahydro-5,5,8,8-tetramethyl-2-naphthalenyl)-2-butenyl-phosphonium bromide, (E) (Compound 25) in 1 ml of tetrahydrofuran, 0.4072 g (0.3791 ml, 2.9 mmol) of ethyl 2-formyl-1-cyclopropane carboxylate (available from Aldrich Chemical Co.) and 9.6 g (11.5 ml, 133.4 mmol) of 1,2-epoxybutane were combined under argon and heated at 70° C. for 72 hours then stirred at room temperature for 24 hours. The resulting solution was concentrated in-vacuo and the residue purified using flash chromatography ( SiO2, 2% ethyl acetate in hexanes) to give a mixture of isomers. To the mixture of isomers in 10 ml of dry ether was added 0.008 g (0.0345 mmol) of iodide at room temperature, exposed to light, stirring for 20 hours to increase the yield of trans, trans isomer (trans about the double bonds). The solvent was removed in-vacuo and the residue purified by flash chromatography (SiO$_2$, 3% ethyl acetate in hexanes). Isomers were separated using HPLC (1% ethyl acetate in hexanes) to give the title compound as a clear oil.

PMR (CDCl$_3$): $\delta$0.84–0.91(1H,m), 1.14–1.32 (16H,m), 1.50–1.56 (1H,m), 1.62(4H,s), 1.82–1.91(1H,m), 2.02(3H,s), 4.03(2H,q), 5.16(1H,dd,J$\sim$15 Hz, J$\sim$9.5 Hz), 5.97(1H,d,J$\sim$12 Hz), 6.28(1H,dd,J$\sim$15 Hz, J$\sim$12 Hz), 7.21(1H,d,J$\sim$8 Hz), 7.10(1H,d,J$\sim$2 Hz), 7.95(1H,dd,J$\sim$8 Hz, J$\sim$2 Hz).

Ethyl trans 2-[4-methyl-4(5,6,7,8-tetrahyro-5,5,8,8-tetramethyl-2-naphthyl) E,E 1-3 butadienyl] 1-cyclopropane carboxylate (Compound 2)

A suspension of 1.67 g (2.5 mmol) of triphenyl[3-(5,6,7,8-tetrahydro-5,5,8,8-tetramethyl-2-naphthalenyl)-2-butenyl-phosphonium bromide, (E) (Compound 25) in 1 ml of tetrahydrofuran, 0.4072 g (0.3791 ml, 2.9 mmol) of ethyl 2-formyl-1-cyclopropane carboxylate and 9.6 g (11.5 ml, 133.4 mmol) of 1,2-epoxybutane were combined under argon and heated at 70° C. for 72 hours then stirred at room temperature for 24 hours. The resulting solution was concentrated in-vacuo and the residue purified using flash chromatography ( SiO2, 2% ethyl acetate in hexanes) to give a mixture of isomers. To the mixture of isomers in 10 ml of dry ether was added 0.008 g (0.0345 mmol) of iodide at room temperature, exposed to light, stirring for 20 hours to increase the yield of trans, trans isomer (trans about the double bonds). The solvent was removed in-vacuo and the residue purified by flash chromatography (SiO2, 3% ethyl acetate in hexanes). Isomers were separated using HPLC (1% ethyl acetate in hexanes) to give the title compound as a clear oil.

PMR (CDCl3): $\delta$1.01–1.09 (1H,m), 1.27–1.31 (15H,m), 1.43–1.50 (1H,m), 1.56–1.57(5H,m), 2.09–2.20(4H,s), 4.16(2H,q), 5.35(1H,dd,J~15 Hz, J~9.0 Hz), 6.37(1H,d,J~11 Hz), 6.62(1H,dd,J~15 Hz, J~11 Hz), 7.21(1H,dd,J~8.3 Hz, J~1.95 Hz), 7.28(1H,d,J~8.3 Hz), 7.37(1H,d, J~1.95 Hz)

Cis-2-[4-methyl-4(5,6,7,8-tetrahyro-5,5,8,8-tetramethylyl-2-naphthyl) E,E 1-3 butadienyl] 1-cyclopropane carboxylic acid (Compound 4)

A solution 0.040 g (0.1093 mmol) of ethyl cis-2-[4-methyl-4(5,6,7,8-tetrahyro-5,5,8,8-tetramethyl-2-naphthyl) E,E 1-3 butadienyl] 1-cyclopropane carboxylate (Compound 1) in 1 ml of methanol and 0.092 g (0.08 ml, 0.1639 mmol) of 2N potassium hydroxide/methanol solution was stirred at reflux under argon for 48 hours. An additional 0.092 g (0.08 ml, 0.1639 mmol) of 2N potassium hydroxide/methanol solution was added to the mixture and refluxed for 24 hours. The mixture was cooled to room temperature and taken up with water and extracted with ether. The aqueous layer was then acidified using 80:20 ETOAc/HCl to PH5, and extracted with ether. The ether extracts were washed with water, brine and dried (MgSO4). The solvent was removed in-vacuo to give the title compound as a yellow solid.

PMR(CDCl3): $\delta$0.97–1.10 (1H,m), 1.20–1.44 (13H,m), 1.56–1.65 (1H,m), 1.70 (4H,s), 2.10 (3H,s), 5.21 (1H,dd,J~15 Hz, J~9.0 Hz), 6.03 (1H,d,J~12 Hz), 6.35 (1H,dd,J~15 Hz, J~12 Hz), 7.0 (1H,dd,J~8 Hz), J~2 Hz), 7.15 (1H,d,J~2 Hz), 7.28 (1H,d,J~8 Hz)

Trans-2-[4-methyl-4(5,6,7,8-tetrahyro-5,5,8,8-tetramethyl-2-naphthyl) E,E 1-3 butadienyl] 1-cyclopropane carboxylic acid (Compound 3)

A solution of 0.80 g (0.4918 mmol) of ethyl trans 2-[4-methyl-4(5,6,7,8-tetrahyro-5,5,8,8-tetramethyl-2-naphthyl) E,E 1-3 butadienyl] 1-cyclopropane carboxylate (Compound 2) in 1 ml of methanol and 0.056 g (0.37 ml, 0.7377 mmol) of 2N potassium hydroxide/methanol solution was stirred at reflux under argon for 36 hours. The mixture was cooled to room temperature and solvent removed in-vacuo. The resulting mixture was cooled to 0° C., acidified using 80:20 ETOAc/HCl to PH3, and extracted with ether. The ether extracts were washed with water, brine and dried (MgSO4). The solvent was removed in-vacuo to give the title compound as a pale yellow solid.

PMR(CDCl3): $\delta$1.10(1H,m), 1.26(6H,m), 1.28(6H,s), 1.50–1.57 (1H,m), 1.65–1.73(5H,m), 2.12–2.26(4H,m), 5.34(1H,dd,J~15 Hz, J~9.0 Hz), 6.36(1H,d,J~12 Hz), 6.63(1H,dd,J~15 Hz, J~12 Hz), 7.21(1H,dd,J~8.3 Hz), J~1.96 Hz), 7.27(1H,d,J~8.3 Hz), 7.37(1H,d,J~1.96 Hz)

Ethyl trans-2-[4-methyl-4(3,5,5,8,8-pentamethyl-5,6,7,8-tetrahyro-2-naphthyl) E,E 1-3 butadienyl] 1-cyclopropane carboxylate (Compound 7)

A suspension of 1 g (1.7 mmol) of triphenyl [3-(5,6,7,8-tetrahydro-3,5,5,8,8,-pentamethyl-2-naphthalenyl)-2-buten-yl] phosphonium bromide (E) (Compound 22) dissolved in 2 ml of tetrahydrofuran, 0.242 g (0.225 ml, 1.7 mmol) of ethyl 2-formyl-1-cyclopropane carboxylate and 5.86 g (7 ml, 81.3 mmol) of 1,2-epoxybutane were combined under argon and heated at 65° C. for 72 hours. The mixture was cooled to room temperature and sovent removed in-vacuo. The residue was purified using flash chromatography (SiO2, 3% ethyl acetate in hexanes) to give a mixture of isomers. To the mixture of isomers in 10 ml of dry ether was added 0.030 g (0.01 mmol) of iodine at room temperature, exposed to light, stirring for 40 hours to increase the yield of the trans isomer. The isomers were sepearated using HPLC (1% ethyl acetate in hexanes) to give the title compound as a clear oil.

PMR (CDCl3): $\delta$1.01–1.06(1H,m), 1.24–1.30(15H,m), 1.42–1.48 (1H,m), 1.65–1.72(5H,m), 2.06(3H,s), 2.08–2.14(1H,m), 2.22(3H,s), 4.15(2H,q), 5.23(1H,dd,J~15.1 Hz, J~9.2 Hz), 5.90(1H,d,J~11.3 Hz), 6.56(1H,dd,J~15.1 Hz, J~11.3 Hz), 7.00(1H,s), 7.07(1H,s)

Ethyl cis-[2-[4-methyl-4-(3,5,5,8,8,-pentamethyl-5,6,7,8-tetrahydronapthalen)-2-yl]-1E,3E-butadien-1-yl] 1-cyclopropane carboxylate (Compound 5)

A suspension of of triphenyl [3-(5,6,7,8-tetrahydro-3,5,5,8,8,-pentamethyl-2-naphthalenyl)-2-buten-yl] phosphonium bromide (E) (1.0 g, 1.7 mmol, Compound 22) dissolved in 2 ml of tetrahydrofuran, ethyl 2-formyl-1-cyclopropane carboxylate (0.242 g 0.225 ml, 1.7 mmol and 1,2-epoxybutane (5.86 g, 7 ml, 81.3 mmol) were combined under argon and heated at 65 C. for 72 hours. The mixture was cooled to room temperature and solvent was removed in-vacuo. The residue was purified using flash chromatography (SiO2, 3% ethyl acetate in hexanes) to give a mixture of isomers. To the mixture of isomers in 10 ml of dry ether was added 30 mg (0.01 mmol) of iodine at room temperature, exposed to light, stirring for 40 hours, in order to increase the yield of the trans isomer about the double bond attached to the cyclopropane ring. Thereafter, the isomers were sepearated using HPLC (1% ethyl acetate in hexanes) to give the title compound as a clear oil.

PMR (CDCl3): 0.87–0.95(1H,m), 1.20–1.38(16H,m), 1.54–1.62 (1H,m), 1.68(4H,s), 1.86–1.94(1H,m), 2.00(3H,s), 2.14(3H,s), 4.09(2H,q), 5.10(1H,dd,J=15.3 Hz, J=9.2 Hz), 5.85(1H,dd,J=15.3 Hz, J=11.0 Hz), 6.03(1H,d, J=11.0 Hz), 6.92(1H,s), 7.09(1H,s)

Cis-[2-[4-methyl-4-(3,5,5,8,8,-pentamethyl-5,6,7,8-tetrahydronapthalen)-2-yl]-1E,3E-butadien-1-yl] 1-cyclopropane carboxylic acid (Compound 6)

A solution of ethyl cis-[2-[4-methyl-4-(3,5,5,8,8,-pentamethyl-5,6,7,8-tetrahydronapthalen)-2-yl]-1E,3E-butadien-1-yl] 1-cyclopropane carboxylate (0.024 g, 0.0632 mmol, Compound 5) in 1 ml of methanol and 5.6 mg (0.05 ml, 0.10 mmol) of 2N potassium hydroxide/methanol solution was stirred at reflux under argon for 48 hours. An additional 5.6 mg (0.05 ml, 0.10 mmol) of 2N potassium hydroxide/methanol solution was added to the mixture and refluxed for 10 hours. The mixture was cooled to room temperature and solvent removed in-vacuo. The resulting mixture was then taken up in water and the aqueous layer was acidified using 80:20 ETOAc/HCl to PH4, and extracted with ether. The ether extracts were washed with water, brine and dried (MgSO4). The solvent was removed in-vacuo to give the title compound as a colorless oil.

PMR (CDCl$_3$): δ0.94–1.00(1H,m), 1.22–1.33(13H,m), 1.58–1.62 (1H,m), 1.70(4H,s), 1.75–1.85(1H,m), 1.99(3H,s), 2.14(3H,s), 5.25(1H,dd,J=15.1 Hz, J=9.3 Hz), 5.84(1H,dd,J=15.1 Hz, J=10.8 Hz), 6.10(1H,d, J=10.8 Hz), 6.98(1H,s), 7.19(1H,s)

Trans-2-[4-methyl-4-(3,5,5,8,8-pentamethyl-5,6,7,8-tetrahyro-2-naphthyl) E,E 1-3 butadienyl] 1-cyclopropane carboxylic acid (Compound 8)

To a solution of 0.2 g (0.084 mmol) of ethyl trans-2-[4-methyl-4(3,5,5,8,8-pentamethyl-5,6,7,8-tetrahyro-2-naphthyl) E,E 1-3 butadienyl] 1-cyclopropane carboxylate (Compound 7) in 0.65 ml (0.084 mmol) of tetrahydrofuran was added 0.336 (0.168 ml) of 0.5M LiOH(aq) dropwise over 1 minute. The solution was stirred for 3 hours at room temperature and at reflux for 18 hours. The mixture was cooled to room temperature and taken up with water and ether. The aqueous layer was cooled to 0° C. and acidified with 10% aq. HCl and extracted with methylene chloride. The combined organic layers were washed with water, brine and dried (MgSO4). Solvent was removed in-vacuo and the residue purified by flash chromatography (SiO2, 3% ethyl acetate in hexanes) to give the title compound as a white powder.

PMR (CDCl$_3$): δ1.11(1H,m), 1.26(6H,s), 1.27(6H,s), 1.51 (1H,m), 1.66(4H,s), 1.67(1H,m), 2.06(3H,s), 2.22(3H,s), 2.22(1H,m) 5.23(1H,dd,J~14.8 Hz, J~8.8 Hz), 5.91 (1H,d, J~11.2 Hz), 6.58(1H,dd, J~14.8 Hz, J~11.2 Hz), 7.01(1H,s), 7.07(1H,s).

What is claimed is:

1. A compound of the formula:

wherein
m is 1-4;
$R_1$–$R_4$ independently are hydrogen, lower alkyl of 1 to 6 carbons, Cl, Br, or I;
$R_5$ is hydrogen, lower alkyl of 1 to 6 carbons, Cl, Br, I, lower alkoxy or lower thioalkoxy of 1–6 carbons;
$R_6$ is hydrogen, lower alkyl, Cl, Br, I, OR$_{11}$, SR$_{11}$, OCOR$_{11}$, SCOR$_{11}$, NH2, NHR$_{11}$, N(R$_{11}$)$_2$, NHCOR$_{11}$ OR NR$_{11}$—COR$_{11}$;
$R_{20}$ is independently hydrogen or lower alkyl;
A is (CH$_2$)$_n$ where n is 0–5, lower branched chain alkyl having 3–6 carbons, cycloalkyl having 3–6 carbons, alkenyl having 2–6 carbons and 1 or 2 double bonds, alkynyl having 2–6 carbons and 1 or 2 triple bonds;
B is hydrogen, COOH or a pharmaceutically acceptable salt thereof, COOR$_8$, CONR$_9$R$_{10}$, —CH$_2$OH, CH$_2$OR$_{11}$, CH$_2$OCOR$_{11}$, CHO, CH(OR$_{12}$)$_2$, CHOR$_{13}$O, —COR$_7$, CR$_7$(OR$_{12}$)$_2$, or CR$_7$OR$_{13}$O, where R$_7$ is an alkyl, cycloalkyl or alkenyl group containing 1 to 5 carbons, R$_8$ is an alkyl group of 1 to 10 carbons, or a cycloalkyl group of 5 to 10 carbons, or R$_8$ is phenyl or lower alkylphenyl, R$_9$ and R$_{10}$ independently are hydrogen, an alkyl group of 1 to 10 carbons, or a cycloalkyl group of 5–10 carbons, or phenyl or lower aklylphenyl, R$_{11}$ is lower alkyl, phenyl or lower alkylphenyl, R$_{12}$ is lower alkyl, and R$_{13}$ is divalent alkyl radical of 2–5 carbons.

2. A compound of claim 1 wherein A is (CH$_2$)$_n$ and n is 0.

3. A compound of claim 1 wherein B is COOH or a pharmaceutically acceptable salt thereof, or B is COOR$_8$.

4. A compound of claim 1 where R$_2$, R$_3$, R$_4$, and R$_5$ are hydrogen.

5. A compound of claim 1 where R$_1$ and R$_{20}$ are methyl.

6. A compound of claim 1 where R$_6$ is methyl or hydrogen.

7. A compound of claim 1 where the configuration about cyclopropane ring is trans.

8. A compound of claim 1 where the configuration about cyclopropane ring is cis.

9. A pharmaceutical composition comprising a pharmaceutically acceptable excipient and one or more compounds set forth in claim 1 as the active ingredient.

10. A method for treating skin disorders in a mammal which method comprises administering alone or in conjunction with a pharmaceutically acceptable excipient a therapeutically effective amount of one or more compounds set forth in claim 1.

11. A compound of the formula wherein R6 is hydrogen, lower alkyl of 1–6 carbons, Cl, Br, or I, and
R$_8$ is hydrogen, or an alkyl group of 1 to 10 carbons.

12. A compound of claim 11 where R$_6$ is hydrogen.

13. A compound of claim 12 where R$_8$ is ethyl.

14. The compound of claim 13 where the configuration is cis about the cyclopropane ring.

15. The compound of claim 13 where the configuration is trans about the cyclopropane ring.

16. A compound of claim 12 where R$_8$ is hydrogen.

17. The compound of claim 16 where the configuration is cis about the cyclopropane ring.

18. The compound of claim 16 where the configuration is trans about the cyclopropane ring.

19. A compound of claim 11 where R$_6$ is methyl.

20. A compound of claim 19 where R$_8$ is ethyl.

21. The compound of claim 20 where the configuration is cis about the cyclopropane ring.

22. The compound of claim 20 where the configuration is trans about the cyclopropane ring.

23. A compound of claim 19 where R$_8$ is hydrogen.

24. The compound of claim 23 where the configuration is cis about the cyclopropane ring.

25. The compound of claim 23 where the configuration is trans about the cyclopropane ring.

* * * * *

UNITED STATES PATENT AND TRADEMARK OFFICE
CERTIFICATE OF CORRECTION

PATENT NO. : 5,344,959

DATED : September 6, 1994

INVENTOR(S) : Roshantha A. Chandraratna

It is certified that error appears in the above-identified patent and that said Letters Patent is hereby corrected as shown below:

Column 3, in Formula 2, "$PPH_3^+Br$" should be --$PPh_3Br^-$--;

Column 5, line 1, "(5,5,8,-tetramethyl" should be --(5,5,8,8-tetramethyl--;

Column 5, line 2, "1 3-butadienyl" should be --1-3-butadienyl--;

Column 5, line 28, "CH3" should be --$CH_3$--;

Column 5, line 44, "ache" should be --acne--;

Column 15, line 19-20, "tetramethylyl" should be --tetramethyl--.

Signed and Sealed this

Ninth Day of May, 1995

BRUCE LEHMAN

*Commissioner of Patents and Trademarks*

*Attest:*

*Attesting Officer*

UNITED STATES PATENT AND TRADEMARK OFFICE
CERTIFICATE OF CORRECTION

PATENT NO. : 5,344,959
DATED : September 6, 1994
INVENTOR(S) : Roshantha A. Chandrartna It is certified that error appears in the above-identified patent and that said Letters Patent is hereby corrected as shown below:

Column 1, line 60, "1-methyl,-1-" should be --1-methyl-1- --;

Column 2, line 17, "NH2" should be --$NH_2$--;

Column 7, line 11, "days" should be --day--;

Colomn 8, line 58, "nap-" should be --naph--;

Column 11, lines 24 and 48, "MgSO4" should be --$MgSO_4$--;

Column 11, line 59, "tetrahydrodnapthalen" should be
    --tetrahydronaphthalen--;

Column 12, line 41, "MgSO4" shuld be --$MgSO_4$--;

Column 12, line 58, "tetrahydrodnapthalen" shuld be
    --tetrahydronaphthalen--;

Column 13, line 63, "MgSO4" should be --$MgSO^4$--;

Column 13, line 65, "SiO2" should be --$SiO_2$--;

Column 14, ine 10-11, "tetrahydtronapthalen" should be
    --tetrahydronaphthalen--;

Column 14, line 37, "SiO2" shuld be --$SiO_2$--;

Column 14, line 68, "SiO2" should be --$SiO_2$--;

Column 15, line 50, "tetrahyro" shuld be --tetrahydro--;

Column 16, line 2-3, "tetrahyro" should be --tetrahydro--;

Column 16, line 14, "sovent" should be --solvent--;

Column 16, line 15, "SiO2" should be --$SiO_2$--;

UNITED STATES PATENT AND TRADEMARK OFFICE
CERTIFICATE OF CORRECTION

PATENT NO. : 5,344,959

DATED : September 6, 1994

INVENTOR(S) : Roshantha A. Chandraratna

It is certified that error appears in the above-identified patent and that said Letters Patent is hereby corrected as shown below:

Column 16, line 31-32, "tetrahydronapthalen" should be --tetrahydronaphthalen--;

Column 16, line 40, "65 C" should be --65° C--;

Column 16, line 43, "SiO2" should be --$SiO_2$--;

Column 16, lines 58 and 62, "tetrahydronapthalen" should be --tetrahydronaphthalen--;

Column 17, line 14, "tetrahyro" should be --tetrahydro--;

Column 17, line 29, "MgSO4" should be --$MgSO_4$--;

Column 17, line 31, "SiO2" should be --$SiO_2$--;

Column 17, line 55, "NH2" should be --$NH_2$--.

Signed and Sealed this

Twenty-fifth Day of July, 1995

BRUCE LEHMAN

*Attest:*

*Attesting Officer*          *Commissioner of Patents and Trademarks*